United States Patent
Lee et al.

(10) Patent No.: US 7,972,987 B2
(45) Date of Patent: Jul. 5, 2011

(54) FOURTH GROUP TRANSITION METAL COMPOUND HAVING CYCLOPENTADIENYL LIGAND, METHOD OF PREPARING COMPOUND, AND METHOD OF PREPARING OLEFIN POLYMER USING COMPOUND

(75) Inventors: Jung-A Lee, Daejeon Metropolitan (KR); Bo-Ram Lee, Seoul (KR); Eun-Jung Lee, Daejeon Metropolitan (KR); Seung-Whan Jung, Suwon-Si (KR); Choong-Hoon Lee, Daejeon Metropolitan (KR)

(73) Assignee: LG Chem, Ltd. (KR)

( * ) Notice: Subject to any disclaimer, the term of this patent is extended or adjusted under 35 U.S.C. 154(b) by 68 days.

(21) Appl. No.: 12/527,091

(22) PCT Filed: Feb. 13, 2008

(86) PCT No.: PCT/KR2008/000832
§ 371 (c)(1),
(2), (4) Date: Aug. 13, 2009

(87) PCT Pub. No.: WO2008/100064
PCT Pub. Date: Aug. 21, 2008

(65) Prior Publication Data
US 2010/0113721 A1    May 6, 2010

(30) Foreign Application Priority Data
Feb. 15, 2007 (KR) .................. 10-2007-0015789

(51) Int. Cl.
*C07F 17/00* (2006.01)
*B01J 31/18* (2006.01)
*B01J 31/22* (2006.01)
*C08F 4/6592* (2006.01)

(52) U.S. Cl. ........ 502/155; 502/103; 502/104; 502/152; 526/133; 526/160; 526/161; 526/165; 526/172; 526/943; 556/53

(58) Field of Classification Search ............. 526/133, 526/160, 161, 165, 172, 943; 556/53; 502/103, 502/104, 152, 155
See application file for complete search history.

(56) References Cited

U.S. PATENT DOCUMENTS

| | | | |
|---|---|---|---|
| 5,986,029 | A | 11/1999 | van Beek et al. |
| 6,437,161 | B1 | 8/2002 | Mihan et al. |
| 2002/0193536 | A1 | 12/2002 | Kashiwamura et al. |
| 2004/0116632 | A1 | 6/2004 | Masi et al. |
| 2007/0225158 | A1 * | 9/2007 | Lee et al. ................. 502/152 |

FOREIGN PATENT DOCUMENTS

WO    93/19104 A1    9/1993

OTHER PUBLICATIONS

Jutzi et al, Journal of Organometallic Chemistry, 533; 237-245 (1997).
Blais et al, Organometallics, 17; 3775-3783 (1998).
Herrmann et al. Journal of Organometallic Chemistry, 486; 291-295 (1995).
Enders et al, Journal of Organometallic Chemistry, 549; 251-256 (1997).
International Search Report, PCT/KR2008/000832, dated Jun. 9, 2008.
Cho et al., Organometallics, 25(9); 2133-2134 (2006).
Enders et al., Journal of Organometallic Chemistry, 641(1-2); 81-89 (2002).

* cited by examiner

*Primary Examiner* — Caixia Lu
(74) *Attorney, Agent, or Firm* — Lerner, David, Littenberg, Krumholz & Mentlik, LLP

(57) ABSTRACT

The present invention relates to a novel cyclopentadienyl compound, a fourth group transition metal compound having the cyclopentadienyl compound, a method of preparing the fourth group transition metal compound, a method of preparing an olefin polymer by using the fourth group transition metal compound, and an olefin polymer prepared by using the method.

12 Claims, No Drawings

FOURTH GROUP TRANSITION METAL COMPOUND HAVING CYCLOPENTADIENYL LIGAND, METHOD OF PREPARING COMPOUND, AND METHOD OF PREPARING OLEFIN POLYMER USING COMPOUND

CROSS REFERENCE TO RELATED APPLICATIONS

The present application is a national phase entry under 35 U.S.C. §371 of International Application No. PCT/KR2008/000832, filed Feb. 13, 2008, which claims the benefit of Korean Patent Application No. 10-2007-0015789, filed Feb. 15, 2007. The disclosures of said applications are incorporated by reference herein.

TECHNICAL FIELD

The present invention relates to a novel cyclopentadienyl compound, a fourth group transition metal compound having the cyclopentadienyl compound, a method of preparing the fourth group transition metal compound, a method of preparing an olefin polymer by using the fourth group transition metal compound, and an olefin polymer prepared by using the method.

This application claims priority from Korean Patent Application No. 10-2007-0015789 filed on Feb. 15, 2007 in the KIPO, the disclosure of which is incorporated herein by reference in its entirety.

BACKGROUND ART

Many types of transition metal compounds having a monocyclopentadienyl ligand to which a functional group such as dialkyl amine is introduced have been suggested (see Document [P. Jutzi et al., Journal of Organometallic Chemistry, 1997, 533, 237-245] and Document [M. S. Blais et al., Organometallics, 1998, 17, 3775-3783]). In the case of when the above dialkyl amine functional group is an additional chain that is connected to a cyclopentadienyl group, the dialkyl amine functional group can be interacted along with a central metal.

In the document made by Herrmann et al. [Journal of Organometallic Chemistry, 1995, 486, 291-195], there is disclosed synthesis of a titanium (IV) compound having a monocyclopentadienyl ligand to which a cyclic alkyl amine functional group such as pyrrolidine and piperidine is introduced. The functional group such as pyrrolidine and piperidine is a ô-donating group, and is synthesized from a trimethylsilylcyclopentadienyl precursor and titanium (IV) tetrachloride.

U.S. Pat. No. 5,986,029 discloses synthesis and polymerization results of a three-valent titanium (III) compound having a monocyclopentadienyl ligand to which various types of dialkyl amine functional groups are introduced. The above patent discloses (dimethylaminoethyl)tetramethylcyclopentadienyl titanium (III) dichloride [($C_5Me_4(CH_2)_2NMe_2TiCl_2$)], (N-pyrrolidinylethyl)tetramethylcyclopentadienyl titanium (III) dichloride [($C_5Me_4(CH_2)_2NC_4H_8TiCl_2$)] and the like as the above three-valent titanium (III) compound.

The document made by Enders et al. [Chem. Ber., 1996, 129, 459-463., Journal of Organometallic Chemistry, 1997, 549, 251-156] discloses synthesis of a titanium (IV) trichloride compound having a cyclopentadienyl ligand of which an 8-quinoline group is substituted and a zirconium (IV) trichloride compound having a cyclopentadienyl ligand of which an pyridine group is substituted. Both the two compounds are synthesized from a trimethylsilylcyclopentadienyl precursor and a titanium (IV) tetrachloride or zirconium (IV) tetrachloride, and from the analysis of a crystal structure, it has been already confirmed that a nitrogen atom of a pyridine group is coordinated with a central metal.

Synthesis and polymerization results of chromium, molybdenum, and tungsten chloride compounds having a monocyclopentadienyl ligand, of which an 8-quinoline group is substituted have been suggested (U.S. Pat. No. 6,437,161).

DISCLOSURE OF INVENTION

Technical Problem

The present inventors have found a novel monocyclopentadienyl compound and a novel fourth group transition metal compound having the monocyclopentadienyl compound, and also found that the compound can be used as a polymerization catalyst of an olefin monomer.

Accordingly, it is an object of the present invention to provide a novel monocyclopentadienyl compound, a novel fourth group transition metal compound, a catalyst composition for polymerizing an olefin monomer, which has the compound, a method of preparing an olefin polymer by using them, and an olefin polymer prepared by using the method.

Technical Solution

In order to accomplish the above object, the present invention provides a fourth group transition metal compound of the following Formula 1 and a method of preparing the same.

[Formula 1]

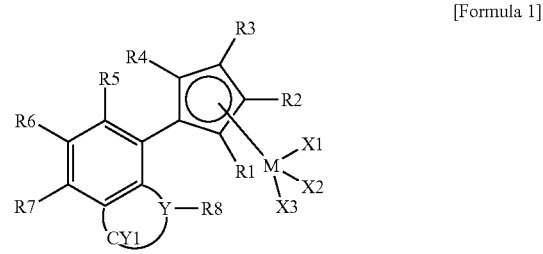

wherein R1 to R4 are the same or different from each other and each independently a hydrogen atom; an alkyl radical having 1 to 20 carbon atoms; an alkenyl radical having 2 to 20 carbon atoms; a silyl radical; an alkylaryl radical; or an arylalkyl radical, and may be connected to each other by an alkylidene radical containing an alkyl radical having 1 to 20 carbon atoms or aryl radical to form a ring, R5 to R7 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R5 to R7 may be connected to each other to form an aliphatic or aromatic ring, R8 is a hydrogen atom; an alkyl radical having 1 to 20 carbon atoms; an aryl radical; an alkylaryl radical; or an arylalkyl radical, and is not present when Y is a sixteenth group atom, CY1 is a substituted or unsubstituted aliphatic or aromatic ring, Y is a fifteenth or sixteenth group atom, M is a fourth group transition metal, and X1 to X3 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

Furthermore, the present invention provides a cyclopentadienyl compound of the following Formula 2 as a ligand used to prepare the fourth group transition metal compound:

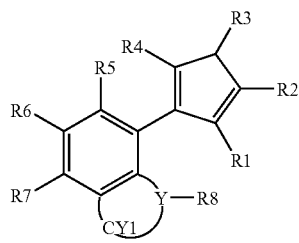

[Formula 2]

wherein R1 to R8, CY1, and Y are the same as those defined in the Formula 1.

In addition, the present invention provides a catalyst composition for polymerizing an olefin monomer that includes a fourth group transition metal compound of the above Formula 1 and a method of preparing an olefin polymer by using the same. Furthermore, the present invention provides an olefin polymer that is polymerized by using the above catalyst composition.

Advantageous Effects

The fourth group transition metal compound according to the present invention is a novel compound. In the case of when the fourth group transition metal compound is used as a catalyst to prepare an olefin polymer, even though a comonomer is an olefin monomer having a high steric hindrance, it is possible to prepare a polymer that has an excellent copolymerization reactivity, a high copolymerization activity and degree of copolymerization at a high temperature of 150° C. or more, a low density, and a high molecular weight.

BEST MODE FOR CARRYING OUT THE INVENTION

Hereinafter, the present invention will be described in detail.

Substituent groups of the above Formula 1 will be described in detail.

An alkyl radical having 1 to 20 carbon atoms includes straight- or branched-chained alkyl radicals.

An alkenyl radical having 2 to 20 carbon atoms includes straight- or branched-chained alkyl radicals.

Examples of a silyl radical include, but are not limited to trimethylsilyl, triethylsilyl, tripropylsilyl, tributylsilyl, trihexylsilyl, triisopropylsilyl, triisobutylsilyl, triethoxysilyl, triphenylsilyl, and tris(trimethylsilyl)silyl.

It is preferable that an aryl radical have 6 to 40 carbon atoms and specific examples of the aryl radical include, but are not limited to phenyl, naphthyl, anthracenyl, pyridyl, dimethyl anilinyl, and anisolyl.

An alkylaryl radical means an aryl radical which is substituted by the alkyl radical.

An arylalkyl radical means an alkyl radical which is substituted by the aryl radical.

A halogen radical means a fluorine group, a chlorine group, a bromine group, or an iodine group.

An alkylamino radical means an amino radical that is substituted by the alkyl radical and examples of the alkylamino radical include, but are not limited to a dimethylamino group and a diethylamino group.

An arylamino radical means an amino radical that is substituted by the aryl radical and examples of the arylamino radical include, but are not limited to a diphenylamino group.

Examples of the 15th group element include, but are not limited to N and P.

Examples of the 16th group element include, but are not limited to O and S.

Examples of the 4th transition metal include Ti, Zr, and Hf.

The compound of the above Formula 1 may be represented by the following Formula 1-1:

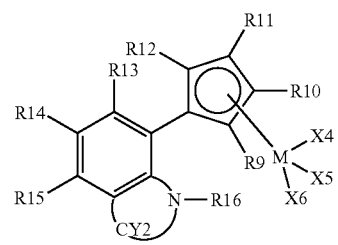

[Formula 1-1]

wherein R9 to R12 are the same or different from each other and each independently a hydrogen atom; an alkyl radical having 1 to 20 carbon atoms; an alkenyl radical having 2 to 20 carbon atoms; a silyl radical; an alkylaryl radical; or an arylalkyl radical, and may be connected to each other by an alkylidene radical containing an alkyl radical having 1 to 20 carbon atoms or aryl radical to form a ring, R13 to R15 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R13 to R15 may be connected to each other to form an aliphatic or aromatic ring, R16 is a hydrogen atom; an alkyl radical having 1 to 20 carbon atoms; an aryl radical; an alkylaryl radical; or an arylalkyl radical, CY2 is a substituted or unsubstituted aliphatic or aromatic ring, M is a fourth group transition metal, and X4 to X6 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

The compound of the above Formula 1 may be preferably a compound represented by the following Formula 1-2 or 1-3:

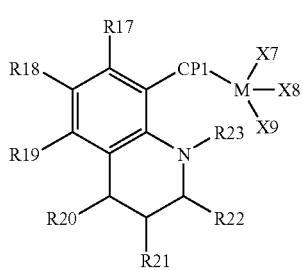

[Formula 1-2]

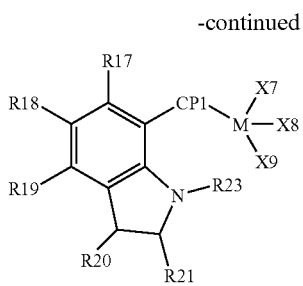

wherein R17 to R22 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R17 to R22 may be connected to each other to form an aliphatic ring having 5 to 20 carbon atoms or an aromatic ring having 6 to 20 carbon atoms, R23 is a hydrogen atom; an alkyl radical having 1 to 20 carbon atoms; an aryl radical having 6 to 20 carbon atoms; an alkylaryl radical; or an arylalkyl radical, CP1 is a cyclopentadienyl group or a derivative thereof, M is a fourth group transition metal, and X7 to X9 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

Examples of CP1 include a cyclopentadienyl group, and examples of a derivative thereof include a cyclopentadienyl group; a tetramethylcyclopentadienyl group; an indenyl group; and a fluorenyl group.

In addition, the present invention provides a cyclopentadienyl compound of the following Formula 2 as a ligand used to prepare the compound of Formula 1:

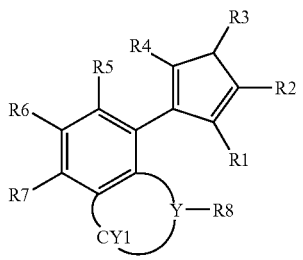

wherein R1 to R8, CY1, and Y are the same as those defined in the Formula 1.

For example, the compound of the above Formula 2 may be represented by the following Formula 2-1:

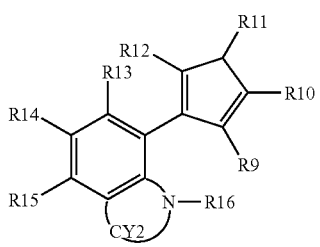

wherein R9 to R16, and CY2 are the same as those defined in the above Formula 1-1.

Additionally, the present invention provides a method of preparing a fourth group transition metal compound of the above Formula 1, which comprises the steps of:

a) reacting a compound represented by the following Formula 3 and alkyl lithium, and then adding a compound containing a protecting group (—R25) thereto to prepare a compound represented by the following Formula 4;

b) reacting a compound represented by the following Formula 4 and alkyl lithium, and then adding a ketone compound represented by the following Formula 5 thereto to prepare a compound represented by the following Formula 6;

c) substituting Y of the compound represented by the following Formula 6 by R8 to obtain a ligand to which a cyclic group connected to a phenylene group represented by the above Formula 2 is introduced; and d) continuously adding 1 equivalent of n-BuLi to the ligand represented by the above Formula 2 to obtain a lithium compound, and reacting the lithium compound and a MCl$_4$ (M=Ti, Zr, or Hf) compound to obtain the fourth group transition metal compound represented by the above Formula 1.

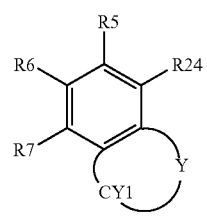

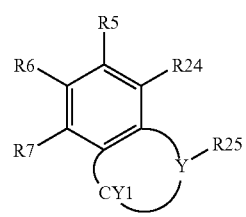

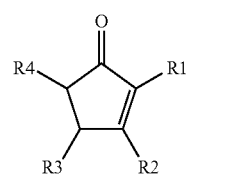

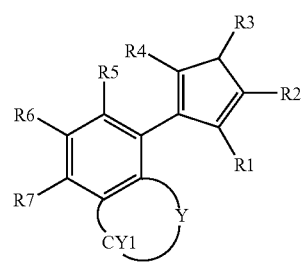

wherein R1 to R7, CY1, and Y are the same as those defined in the above Formula 1, R24 is a hydrogen atom; an alkyl radical having 1 to 20 carbon atoms; an alkenyl radical having 2 to 20 carbon atoms; a silyl radical; an alkylaryl radical; or an arylalkyl radical, and R25 is a protecting group.

The compound that includes the above protecting group (—R25) may be at least one compound which is selected from the group consisting of trimethylsilyl chloride, benzyl chloride, tert-butoxycarbonyl chloride, benzyloxycarbonyl chloride, carbon dioxide and the like.

In the case of when the compound including the above protecting group is carbon dioxide, the lithium compound of the above step d) may be a lithium carbamate compound represented by the following Formula 7:

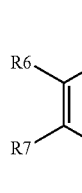

[Formula 7]

wherein R5 to R7, R24, CY1, and Y are the same as those defined in the above Formulae 3 to 6.

For example, the compound of the above Formula 1 may be prepared by using the method which includes a) adding 1 equivalent of n-BuLi and an excessive amount of $CO_2$ gas to 1,2,3,4-tetrahydroquinoline to prepare a lithium carbamate compound, b) adding t-BuLi and a substituted or unsubstituted cyclopentinone compound to the above lithium carbamate compound to prepare a cyclopentadienyl compound, c) substituting a nitrogen atom of the above cyclopentadienyl compound by an alkyl group, an aryl group, an alkylaryl group, or an arylalkyl group to obtain a ligand to which a cyclic amine functional group connected to the phenylene group is introduced, and d) continuously adding 1 equivalent of n-BuLi to the above ligand to obtain a lithium compound, and reacting the lithium compound and the $MCl_4$ (M=Ti, Zr, or Hf) compound to obtain the fourth group transition metal compound.

The preparation method may be performed by using the following Reaction Equation.

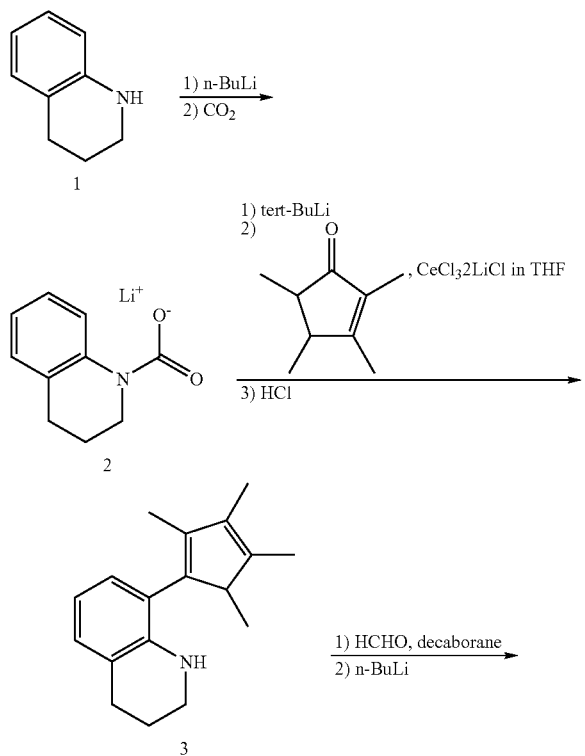

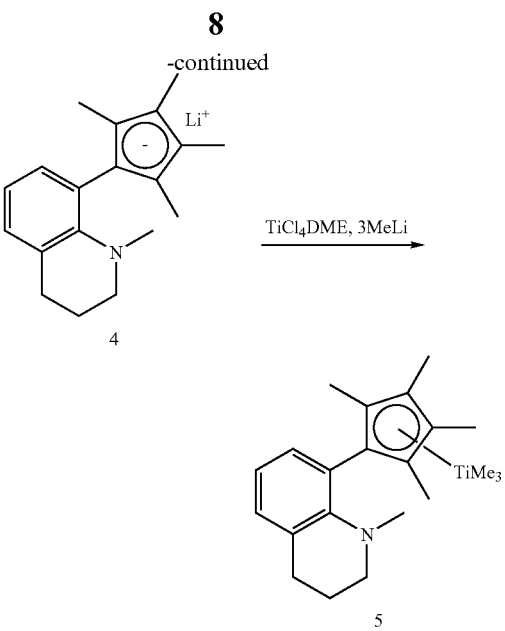

Additionally, the method of preparing a transition metal compound according to the present invention may skip the step a), when Y of the Chemical Formula 1 is a sixteenth group atom.

The present invention also provides a catalyst composition for polymerizing an olefin monomer, which includes the compound represented by the above Formula 1.

The catalyst composition may include one or more cocatalyst compounds among compounds represented by the following Formulae 8 to 10 in addition to the fourth group transition metal compound of the above Formula 1.

$$—[Al(R26)-O]_n—$$ [Formula 8]

wherein R26s may be the same or different from each other and each independently a halogen group, a hydrocarbon group having 1 to 20 carbon atoms, or a hydrocarbon group which is substituted by halogen and has 1 to 20 carbon atoms, and n is an integer of 2 or more.

$$D(R26)_3$$ [Formula 9]

wherein R26 is the same as that defined in the above Formula 8 and D is aluminum or boron.

$$[L-H]^+[ZA_4]^- \text{ or } [L]^+[ZA_4]^-$$ [Formula 10]

wherein L is a neutral or cationic Lewis acid, H is a hydrogen atom, Z is a thirteenth group element, and As may be the same or different from each other and each independently aryl having 6 to 20 carbon atoms or alkyl having 1 to 20 carbon atoms, of which one or more hydrogen atoms are unsubstituted or substituted by a halogen group, a hydrocarbon group having 1 to 20 carbon atoms, alkoxy, or phenoxy.

Examples of the compound represented by the above Formula 8 include methylaluminoxane, ethylaluminoxane, isobutylaluminoxane, and butylaluminoxane, and it is more preferable to use methylaluminoxane.

Examples of the compound represented by the above Formula 9 include trimethylaluminum, triethylaluminum, triisobutylaluminum, tripropylaluminum, tributylaluminum, dimethylchloroaluminum, triisopropylaluminum, tris-butylaluminum, tricyclopentylaluminum, tripentylaluminum, triisopentylaluminum, trihexylaluminum, trioctylaluminum, ethyldimethylaluminum, methyl-diethylaluminum, triphenylaluminum, tri-p-tolylaluminum, dimethylaluminum methoxide, dimethylaluminum ethoxide, trimethylboron, triethylboron, triisobutylboron, tripropylboron, and tributylboron, and it is more preferable that the compound be selected from trimethylaluminum, triethylaluminum, and triisobutylaluminum.

Examples of the compound represented by the above Formula 10 include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylanilidiumtetraphenylboron, N,N-diethylanilidiumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, tripropylammoniumtetra(p-tolyl)boron, triethylammoniumtetra(o,p-dimethylphenyl)boron, tributylammoniumtetra(p-trifluoromethylphenyl)boron, N,N-diethylaniliniumtetraphenylboron, triphenylcarboniumtetra(p-trifluoromethylphenyl)boron, and triphenylcarboniumtetrapentafluorophenylboron.

The above catalyst composition may be prepared by using the method which includes 1) bringing the fourth group transition metal compound of the above Formula 1 into contact with the compound represented by the above Formula 8 or 9 to obtain a mixture, and 2) adding the compound represented by the above Formula 10 to the mixture. In addition, the above catalyst composition may be prepared by using the method which includes bringing the fourth group transition metal compound represented by the above Formula 1 into contact with the compound represented by the above Formula 8.

During the preparation of the catalyst composition including the fourth group transition metal compound of the above Formula 1, a hydrocarbon solvent such as pentane, hexane, and heptane or an aromatic solvent such as benzene and toluene may be used as the reaction solvent. In addition, the transition metal compound and the cocatalyst may be used while being carried in silica or alumina.

Furthermore, the present invention provides a method of preparing an olefin polymer by using the catalyst composition including the compound of the above-mentioned Formula 1 and an olefin polymer prepared by using the method.

The method of preparing the olefin polymer by using the catalyst composition according to the present invention may be a typical method which is known in the related art, except that the fourth group transition metal compound of the above-mentioned Formula 1 is used.

Examples of the available olefin monomer or comonomer may include ethylene, alpha-olefin, and cyclic olefin, and diene olefin monomers or triene olefin monomers having two or more double bonds may be used.

Specific examples of the above monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methyl styrene, divinylbenzene, and 3-chloromethyl styrene, and two or more monomers may be mixed with each other to be copolymerized.

Ethylene and 1-butene are copolymerized by using the fourth group transition metal compound of the above Formula 1 according to the present invention to obtain a copolymer having a high molecular weight and a low density. The results can be seen from Examples and Comparative Examples as described later. The results mean that the copolymerization reactivity of the catalyst composition according to the present invention is excellent in the case of the olefin monomer having a high steric hindrance such as 1-butene. Additionally, in general, it is known that the mixing of the co-monomers is reduced as the temperature is increased. In the case of the catalyst composition included in the present invention, a polymer that has the excellent copolymerization activity and degree of copolymerization, the low density, and the high molecular weight can be prepared at the high polymerization temperature of 150° C. or more. From the results, it can be said that the transition metal compound and the catalyst composition using the same included in the present invention are useful to prepare a copolymer having a low density and a high molecular weight at a high temperature of about 150° C. or more.

Mode for the Invention

A better understanding of the present invention may be obtained in light of the following Examples which are set forth to illustrate, but are not to be construed to limit the present invention.

EXAMPLE/COMPARATIVE EXAMPLE

<Synthesis of the Ligand and the Transition Metal Compound>

The organic reagent and the solvent were bought from Aldrich, Co. and Merck, Co., Ltd. and then purified by using a standard method. At all the steps of the synthesis, air was prevented from coming into contact with water in order to increase the reproducibility of the test. In order to prove the structure of the compound, the spectrum was obtained by using a nuclear magnetic resonance (NMR) device of 400 MHz.

Example 1

1) Preparation of the lithium carbamate Compound 1,2,3,4-tetrahydroquinoline (13.08 g, 98.24 mmol) and diethyl ether (150 mL) were put in a Schlenk flask. The flask was put in a low temperature bath having the temperature of −78° C. which included dry ice and acetone and agitated for 30 min, and n-butyllithium (39.3 mL, 2.5M hexane solution, 98.24 mmol) was added in a nitrogen atmosphere by using the syringe. The light yellow slurry was formed. After the agitation for 2 hours, the temperature was increased to normal temperature while the formed butane gas was removed. After the flask was put in a low temperature bath having the temperature of −78° C. to reduce the temperature, $CO_2$ gas was added. While the carbon dioxide gas was added, the slurry was removed and the transparent solution was obtained. The flask was connected to the bubbler to increase the temperature to normal temperature while the carbon dioxide gas was removed, and the remaining $CO_2$ gas and the solvent were removed in a vacuum. The flask was transported to the dry box, pentane was added thereto, the agitation was performed, and the filtration was performed to obtain a white solid compound. Diethyl ether was coordinated, and the yield was 100%.

$^1$H NMR ($C_6D_6$, $C_5D_5N$): δ 8.35 (d, J=8.4 Hz, 1H, CH), δ 6.93-6.81 (m, 2H, CH), 6.64 (t, J=7.4 Hz, 1H, CH), δ 3.87 (br, s, 2H, quin-$CH_2$), δ 3.25 (q, J=7.2 Hz, 4H, ether), δ 2.34 (br s, 2H, quin-$CH_2$), δ 1.50 (br s, 2H, quin-$CH_2$), δ 1.90 (t, J=7.2 Hz, 6H, ether) ppm.

2) Preparation of 8-(2,3,4,5-tetramethyl-1,3-cyclopentadienyl)-1,2,3,4-tetrahydroquinoline The prepared lithium carbamate compound (8.47 g, 42.60 mmol) was put in the Schlenk flask. Tetrahydrofuran (4.6 g, 63.9 mmol) and 45 mL of diethyl ether were sequentially added. After the flask was put in a low temperature bath having the temperature of −20° C. which included acetone and a small amount of dry ice and then agitated for 30 min, tert-BuLi (25.1 mL, 1.7M, 42.60 mmol) were added thereto. At this time, the color of the resulting substance was changed to the red color. While the temperature was maintained at −20° C., the agitation was performed for 6 hours. The $CeCl_3.2LiCl$ solution (129 mL, 0.33M, 42.60 mmol) and tetramethylcyclopentinone (5.89 g, 42.60 mmol) which were dissolved in tetrahydrofuran were mixed with each other in the syringe, and then added to the flask in a nitrogen atmosphere. The temperature was slowly increased to normal temperature. After 1 hour, the thermostat was removed to increase the temperature to normal temperature. After water (15 mL) was added, ethyl acetate was added and then filtered to obtain a filtrate solution. The filtrate solution was transported to the separatory funnel and a hydrochloric acid (2N, 80 mL) was added and then shaken for 12 min. Additionally, the saturated sodium hydrogen carbonate aqueous solution (160 mL) was added to perform neutralization, and the organic layer was extracted. Anhydrous magnesium sulfate was added to the organic layer to remove water and perform the filtration, the filtrate solution was taken, and the solvent was removed. The yellow oil was obtained by using a column chromatography. Hexane:toluene (v/v, 10:1). Hexane:ethyl acetate (v/v, 10:1). The yield was 40%.

$^1$H NMR($C_6D_6$): δ 1.00 (br d, 3H, Cp-$CH_3$), 1.63-1.73 (m, 2H, quin-$CH_2$), 1.80 (s, 3H, Cp-$CH_3$), 1.81 (s, 3H, Cp-$CH_3$), 1.85 (s, 3H, Cp-$CH_3$), 2.64 (t, J=6.0 Hz, 2H, quin-$CH_2$), 2.84-2.90 (br, 2H, quin-$CH_2$), 3.06 (br s, 1H, Cp-H), 3.76 (br s, 1H, N—H), 6.77 (t, J=7.2 Hz, 1H, quin-CH), 6.92 (d, J=2.4 Hz, 1H, quin-CH), 6.94 (d, J=2.4 Hz, 1H, quin-CH) ppm.

3) Preparation of lithium 1-(N-methyl-1,2,3,4-tetrahydroquinoline-8-yl)-2,3,4,5-tetramethylcyclopentadienyl The 37% formaldehyde aqueous solution (0.88 mL, 11.8 mmol) was added to the solution in which the prepared 8-(2,3,4,5-tetramethyl-1,3-cyclopentadienyl)-1,2,3,4-tetrahydroquinoline (2 g, 7.89 mmol) was dissolved in methanol (42 mL), and the agitation was performed at normal temperature for 30 min. Decaborane (0.29 g, 2.37 mmol) was added to the mixture and the additional agitation was performed at normal temperature for 1 hour. The prepared compound was filtered by using the hexane and ethyl acetate (v:v=10:1) solvents in respects to the silica pad. The compound which was obtained by removing the filtered solvent of the solution was transported to the flask, pentane (50 mL) was added thereto, and the temperature was reduced to −78° C. n-butyllithium (3.2 mL, 2.5M hexane solution, 7.89 mmol) was added to the syringe in a nitrogen atmosphere at −78° C. After the temperature was slowly increased to normal temperature, the additional agitation was performed at normal temperature for 3 hours. The reactant was filtered in a nitrogen atmosphere and washed with pentane (10 mL) twice, and dried in a vacuum. The yellow solid lithium salt was obtained (0.837 g, 39%).

$^1$H NMR (pyr-d5): δ 7.31 (br s, 1H, CH), δ 7.10-6.90 (m, 1H, CH), δ 6.96 (s, 1H, CH), δ 3.09 (m, 2H, quinoline-$CH_2$), δ 2.77 (t, J=6Hz, 2H, quinoline-$CH_2$), δ 2.51-1.11 (m, 15H, Cp-$CH_3$, N—$CH_3$), δ 1.76 (m, 2H, quinoline-$CH_2$) ppm.

4) Preparation of 1-(N-methyl-1,2,3,4-tetrahydroquinoline-8-yl)-2,3,4,5-tetramethylcyclopentadienyl titanium (IV) trichloride While $TiCl_4.DME$ (429 mg, 1.53 mmol) and diethyl ether (25 mL) were put in the flask in the dry box and agitated at −30° C., MeLi (2.9 mL, 1.6M diethyl ether solution, 4.60 mmol) was slowly added thereto. After the agitation was performed for 15 min, the prepared lithium salt compound (lithium 1-(N-methyll-1,2,3,4-tetrahydroquinoline-8-yl)-2,3,4,5-tetramethylcyclopentadienyl, 419 mg, 1.53 mmol) was added to the flask. While the temperature was increased to normal temperature, the agitation was performed for 3 hours. After the reaction was finished, the solvent was removed in a vacuum, dissolved in pentane, and filtered to extract the filtrate solution. Pentane was removed in a vacuum to obtain a titanium complex (431 mg, 75%).

$^1$H NMR($C_6D_6$): δ 6.83 (d, J=7.2 Hz, 1H, CH), δ 6.78 (d, J=7.6 Hz, 1H, CH), δ 6.73 (t, J=7.4 Hz, 1H, CH), δ 2.80 (m, 2H, quin-$CH_2$), δ 2.52 (t, J=6.4 Hz, 2H, quin-$CH_2$), δ 2.26 (s, 3H, N—$CH_3$), δ 1.96 (s, 6H, Cp-$CH_3$), δ 1.85 (s, 6H, Cp-$CH_3$), δ 1.50 (m, 2H, quin-$CH_2$), δ 1.26 (s, 9H, Ti—$CH_3$) ppm.

Example 2

1) Preparation of 6-methyl-8-(2,3,4,5-tetramethyl-1,3-cyclopentadienyl)-1,2,3,4-tetrahydroquinoline The lithium carbamate compound and 6-methyl-8-(2,3,4,5-tetramethyl-1,3-cyclopentadienyl)-1,2,3,4-tetrahydroquinoline were prepared by using 6-methyl-1,2,3,4-tetrahydroquinoline according to the same method as the above Example 1. The yield was 34%.

$^1$H NMR ($CDCl_3$): δ 6.70 (s, 1H, CH), δ 6.54 (s, 1H, CH), δ 3.71 (br s, 1H, NH), δ 3.25-3.05 (m, 3H, Cp-CH, quinoline-$CH_2$), δ 2.76 (t, J=6.4 Hz, 2H, quinoline-$CH_2$), δ 2.19 (s, 3H, $CH_3$), δ 1.93-1.86 (m, 2H, quinoline-$CH_2$), δ 1.88 (s, 3H, Cp-$CH_3$), δ 1.84 (s, 3H, Cp-$CH_3$), δ 1.74 (s, 3H, Cp-$CH_3$), δ 0.94 (br d, J=6.8 Hz, 3H, Cp-$CH_3$) ppm.

2) Preparation of lithium 1-(6,N-dimethyl-1,2,3,4-tetrahydroquinoline-8-yl)-2,3,4,5-tetramethylcyclopentadienyl Lithium 1-(6,N-dimethyl-1,2,3,4-tetrahydroquinoline-8-yl)-2,3,4,5-tetramethylcyclopentadienyl was prepared by using 6-methyl-8-(2,3,4,5-tetramethyl-1,3-cyclopentadienyl)-1,2,3,4-tetrahydroquinoline according to the same method as the above Example 1.

$^1$H NMR (pyr-d5): δ 7.05 (br s, 1H, CH), δ 6.73 (s, 1H, CH), δ 6.96 (s, 1H, CH), δ 3.08 (m, 2H, quinoline-CH$_2$), δ 2.76 (t, J=6.4 Hz, 2H, quinoline-CH$_2$), δ 2.57-2.25 (m, 18H, Cp-CH$_3$, Ph-CH$_3$, N—CH$_3$), δ 1.76 (m, 2H, quinoline-CH$_2$) ppm.

3) Preparation of 1-(6,N-dimethyl-1,2,3,4-tetrahydroquinoline-8-yl)-2,3,4,5-tetramethylcyclopentadienyl titanium (IV) trichloride 1-(6,N-dimethyl-1,2,3,4-tetrahydroquinoline-8-yl)-2,3,4,5-tetramethylcyclopentadienyl titanium (IV) trichloride was prepared by using the prepared lithium salt compound (lithium 1-(N-methyl1-1,2,3,4-tetrahydroquinoline-8-yl)-2,3,4,5-tetramethylcyclopentadienyl) according to the same method as the above Example 1.

$^1$H NMR (C$_6$D$_6$): δ 6.65 (m, 2H, CH), δ 2.83 (m, 2H, quin-CH$_2$), δ 2.54 (t, J=7.2 Hz, 2H, quin-CH$_2$), δ 2.28 (s, 3H, N—CH$_3$), δ 2.14 (s, 3H, Ph-CH$_3$), δ 1.99 (s, 6H, Cp-CH$_3$), δ 1.87 (s, 6H, Cp-CH$_3$), δ 1.52 (m, 2H, quin-CH$_2$), δ 1.28 (s, 9H, Ti—CH$_3$) ppm Comparative Example 1

Dimethylsilyl(tetramethylcyclopentadienyl)(t-butylamido)titanium (IV) dimethyl Compound The dimethylsilyl(tetramethylcyclopentadienyl)(t-butylamido)titanium (IV) dimethyl compound was prepared by reacting di-methylsilyl(tetramethylcyclopentadienyl)(t-butylamido)titanium (IV) dichloride manufactured by Boulder Scientific, Co., Ltd. in the USA with methyl lithium.

<High Pressure Ethylene and 1-butene Copolymerization>

The compounds which were prepared in the above Example 1 and the above Comparative Example 1 were used as the transition metal compounds to perform C2-C4 copolymerization. Next, physical properties were measured, and the results are described in the following Table 1.

Specifically, after the hexane (1.0 L) solvent and 1-butene (0.8M, 1.2M or 1.6M) were added to a 2 L autoclave reactor, the reactor was preheated so that the temperature of the reactor was as shown in the following Table 1. In addition, in respects to the pressure of the reactor, the reactor was charged with ethylene (35 bar). After 2 mL of 5 10$^{-4}$ M titanium compound which was treated with the triisobutylaluminum compound was put in the tank for storing the catalyst, argon gas at high pressure was applied to the tank so that the compounds were provided into the reactor, and 3 mL of 1 10$^{-3}$ M dimethylanilinium tetrakis(pentafluorophenyl) borate cocatalyst was provided into the reactor by applying the argon gas at high pressure. Ethylene was continuously injected in order to maintain the pressure in the reactor at 34 to 35 bar so that the polymerization reaction was performed for 8 min. The reaction heat was removed by using a cooling coil that is provided in the reactor in order to maintain the polymerization temperature as constant as possible. After the copolymerization reaction was performed for 8 min, the residual ethylene gas was removed, the polymer solution was discharged to the lower part of the reactor, and added to an excessive amount of ethanol to perform cooling, thus obtaining the precipitation. The resulting polymer was washed with ethanol and acetone two to three times and dried in a vacuum oven at 80° C. for 12 hours, and the physical properties were then measured.

The melt index (MI) of the polymer was measured by using ASTM D-1238 (condition E, 190° C., 2.16 Kg load). In addition, the sample which was treated with an antioxidizing agent (1,000 ppm) was processed by using the press mold at 180° C. to form a sheet having a thickness of 3 mm and a radius of 2 cm, and then cooled at a rate of 10° C./min to measure the density of the polymer by using the Mettler balance. 10 mg of the sample was dissolved at the high temperature (100° C.) in conjunction with the solvent (1,1,2,2-Tetrachloroethane-d$_2$) and the content of the comonomer was measured and then analyzed by using the Bruker DRX 600 MHz NMR Spectrometer.

TABLE 1

| | | Copolymerization result of ethylene and 1-butene | | | | | |
|---|---|---|---|---|---|---|---|
| Test No. | Used transition metal compound | Butene (M) | Polymerization temperature (° C.) | Weight of polymer (g) | Melt index$^a$ (g/10 min) | Density (g/cc) | Activity (Kg/g Ti) | Butene conversion ratio (%) |
| 1 | Example 1 | 0.8 | 120 to 163 | 60.01 | 0/0.16 | 0.889 | 1253 | 20.13 |
| 2 | Example 1 | 0.8 | 150 to 170 | 31.13 | 0.13/2.1 | 0.885 | 650 | 11.82 |
| 3 | Example 1 | 1.2 | 120 to 167 | 66.87 | 0/1.4 | 0.873 | 1397 | 21.99 |
| 4 | Example 1 | 1.2 | 150 to 169 | 30.87 | 0.8/8.8 | 0.866 | 645 | 11.57 |
| 5 | Example 1 | 1.6 | 120 to 160 | 67.14 | 0.42/4.8 | 0.866 | 1402 | 18.10 |
| 6 | Example 1 | 1.6 | 150 to 167 | 33.48 | 3/26.1 | 0.860 | 699 | 9.98 |
| 7 | Comparative Example 1 | 1.6 | 120 to 163 | 61.95 | 0.6/8.4 | 0.900 | 1294 | 5.85 |
| 8 | Comparative Example 1 | 1.6 | 150 to 170 | 30.47 | 5.5/59 | 0.903 | 636 | 2.28 |

$^a$I$_2$/I$_{10}$ value

The invention claimed is:

1. A fourth group transition metal compound of the following Formula 1:

[Formula 1]

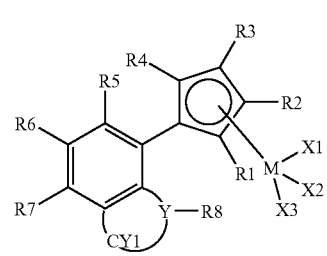

wherein R1 to R4 are the same or different from each other and each independently a hydrogen atom; an alkyl radical having 1 to 20 carbon atoms; an alkenyl radical having 2 to 20 carbon atoms; a silyl radical; an alkylaryl radical; or an arylalkyl radical, and may be connected to each other by an alkylidene radical containing an alkyl radical having 1 to 20 carbon atoms or aryl radical to form a ring, R5 to R7 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R5 to R7 may be connected to each other to form an aliphatic or aromatic ring, R8 is a hydrogen atom; an alkyl radical having 1 to 20 carbon atoms; an aryl radical; an alkylaryl radical; or an arylalkyl radical, and is not present when Y is a sixteenth group atom, CY1 is a substituted or unsubstituted aliphatic or aromatic ring, Y is a fifteenth or sixteenth group atom, M is a fourth group transition metal, and X1 to X3 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

2. The fourth group transition metal compound according to claim 1, wherein the compound of Formula 1 is a compound represented by Formula 1-1:

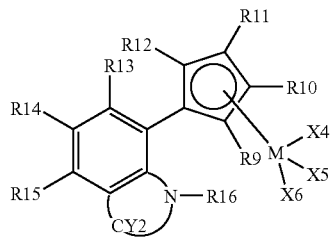

[Formula 1-1]

wherein R9 to R12 are the same or different from each other and each independently a hydrogen atom; an alkyl radical having 1 to 20 carbon atoms; an alkenyl radical having 2 to 20 carbon atoms;

a silyl radical; an alkylaryl radical; or an arylalkyl radical, and may be connected to each other by an alkylidene radical containing an alkyl radical having 1 to 20 carbon atoms or aryl radical to form a ring, R13 to R15 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R13 to R15 may be connected to each other to form an aliphatic or aromatic ring, R16 is a hydrogen atom; an alkyl radical having 1 to 20 carbon atoms; an aryl radical; an alkylaryl radical; or an arylalkyl radical, CY2 is a substituted or unsubstituted aliphatic or aromatic ring, M is a fourth group transition metal, and X4 to X6 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

3. The fourth group transition metal compound according to claim 1, wherein the compound of Formula 1 is a compound represented by Formula 1-2 or 1-3:

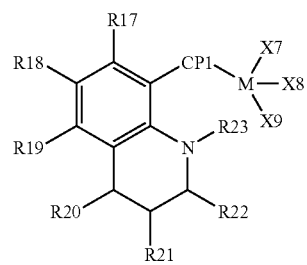

[Formula 1-2]

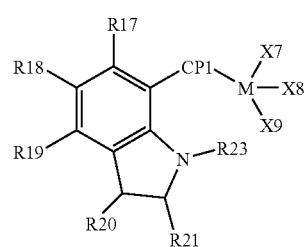

[Formula 1-3]

wherein R17 to R22 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R17 to R22 may be connected to each other to form an aliphatic ring having 5 to 20 carbon atoms or an aromatic ring having 6 to 20 carbon atoms, R23 is a hydrogen atom; an alkyl radical having 1 to 20 carbon atoms; an aryl radical having 6 to 20 carbon atoms; an alkylaryl radical; or an arylalkyl radical, CP1 is a cyclopentadienyl group or a derivative thereof, M is a fourth group transition metal, and X7 to X9 are the same or different from each other and each independently a halogen radical; an alkyl radical having 1 to 20 carbon atoms; an alkenyl radical; an aryl radical; an alkylaryl radical; an arylalkyl radical; an alkylamino radical; an arylamino radical; or an alkylidene radical having 1 to 20 carbon atoms.

4. A compound of the following Formula 2:

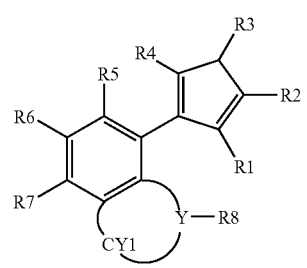

[Formula 2]

wherein R1 to R4 are the same or different from each other and each independently a hydrogen atom; an alkyl radical having 1 to 20 carbon atoms; an alkenyl radical having 2 to 20 carbon atoms; a silyl radical; an alkylaryl radical; or an arylalkyl radical, and may be connected to each other by an alkylidene radical containing an alkyl radical having 1 to 20 carbon atoms or aryl radical to form a ring, R5 to R7 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R5 to R7 may be connected to each other to form an aliphatic or aromatic ring, R8 is a hydrogen atom; an alkyl radical having 1 to 20 carbon atoms; an aryl radical; an alkylaryl radical; or an arylalkyl radical, and is not present when Y is a sixteenth group atom, CY1 is a substituted or unsubstituted aliphatic or aromatic ring, and Y is a fifteenth or sixteenth group atom.

5. The compound according to claim 4, wherein the compound of the above Formula 2 may be a compound represented by the following Formula 2-1:

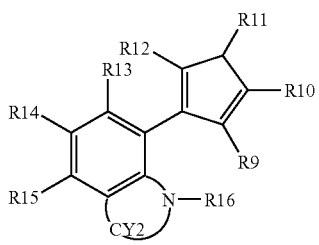

[Formula 2-1]

wherein R9 to R12 are the same or different from each other and each independently a hydrogen atom; an alkyl radical having 1 to 20 carbon atoms; an alkenyl radical having 2 to 20 carbon atoms;

a silyl radical; an alkylaryl radical; or an arylalkyl radical, and may be connected to each other by an alkylidene radical containing an alkyl radical having 1 to 20 carbon atoms or aryl radical to form a ring, R13 to R15 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R13 to R15 may be connected to each other to form an aliphatic or aromatic ring, R16 is a hydrogen atom; an alkyl radical having 1 to 20 carbon atoms; an aryl radical; an alkylaryl radical; or an arylalkyl radical, and CY2 is a substituted or unsubstituted aliphatic or aromatic ring.

6. A method of preparing a fourth group transition metal compound, comprising the steps of:

a) reacting a compound represented by the following Formula 3 and alkyl lithium, and then adding a compound containing a protecting group (—R25) thereto to prepare a compound represented by the following Formula 4;

b) reacting a compound represented by the following Formula 4 and alkyl lithium, and then adding a ketone compound represented by the following Formula 5 thereto to prepare a compound represented by the following Formula 6;

c) substituting Y of the compound represented by the following Formula 6 by R8 to obtain a ligand to which a cyclic group connected to a phenylene group represented by the following Formula 2 is introduced; and d) continuously adding 1 equivalent of n-BuLi to the ligand represented by the following Formula 2 to obtain a lithium compound, and reacting the lithium compound and a $MCl_4$ (M = Ti, Zr, or Hf) compound to obtain the fourth group transition metal compound:

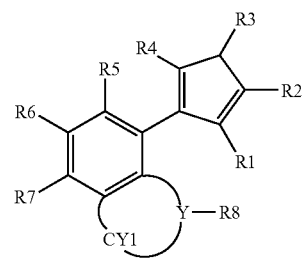

[Formula 2]

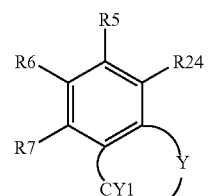

[Formula 3]

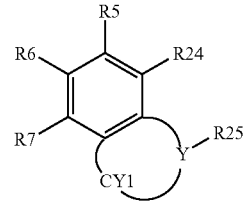

[Formula 4]

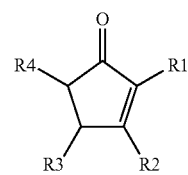

[Formula 5]

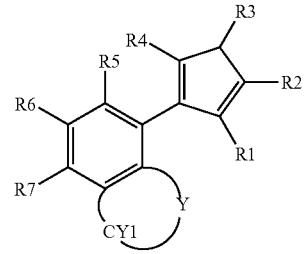

[Formula 6]

wherein R1 to R4 are the same or different from each other and each independently a hydrogen atom; an alkyl radical having 1 to 20 carbon atoms; an alkenyl radical having 2 to 20 carbon atoms; a silyl radical; an alkylaryl radical; or an arylalkyl radical, and may be connected to each other by an alkylidene radical containing an alkyl radical having 1 to 20 carbon atoms or aryl radical to form a ring, R5 to R7 are the same or different from each other and each independently a hydrogen atom; a halogen radical; an alkyl radical having 1 to 20 carbon atoms; an aryl radical; an alkoxy radical; an aryloxy radical; an alkylamino radical; or an arylamino radical, and two or more groups of R5 to R7 may be connected to each other to form an aliphatic or aromatic ring, CY1 is a substituted or unsubstituted aliphatic or aromatic ring, Y is a fifteenth or sixteenth group atom, R8 is a hydrogen atom; an alkyl radical having 1 to 20 carbon atoms; an aryl radical; an alkylaryl radical; or an arylalkyl radical, and is not present when Y is a sixteenth group atom, R24 is a hydrogen atom; an alkyl radical having 1 to 20 carbon atoms; an alkenyl radical having 2 to 20 carbon atoms; a silyl radical; an alkylaryl radical; or an arylalkyl radical, and R25 is a protecting group.

7. The method of preparing a fourth group transition metal compound according to claim 6, wherein the compound containing the protecting group of the above step a) includes at least one which is selected from the group consisting of trimethylsilyl chloride, benzyl chloride, tert-butoxycarbonyl chloride, benzyloxycarbonyl chloride, and carbon dioxide.

8. The method of preparing a fourth group transition metal compound according to claim 6, wherein when the compound containing the protecting group of the above step a) is carbon dioxide, the lithium compound of the above step d) is a lithium carbamate compound represented by the following Formula 7:

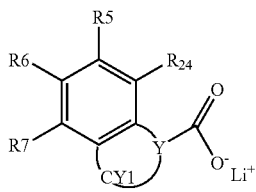

[Formula 7]

wherein R5 to R7, R24, CY1, and Y are the same as those defined in the above Formulae 3 to 6.

9. A catalyst composition for polymerizing an olefin monomer that includes the fourth group transition metal compound of claim 1.

10. The catalyst composition for polymerizing an olefin monomer according to claim 9, further comprising one or more compounds represented by the following Formulae 8 to 10:

—[Al(R26)-O]$_n$—     [Formula 8]

wherein R26s may be the same or different from each other and each independently a halogen group, a hydrocarbon group having 1 to 20 carbon atoms, or a hydrocarbon group which is substituted by halogen and has 1 to 20 carbon atoms, and n is an integer of 2 or more:

D(R26)$_3$     [Formula 9]

wherein R26 is the same as that defined in the above Formula 8 and D is aluminum or boron:

[L-H]$^+$[ZA$_4$]$^-$ or [L]$^+$[ZA$_4$]$^-$     [Formula 10]

wherein L is a neutral or cationic Lewis acid, H is a hydrogen atom, Z is a thirteenth group element, and As may be the same or different from each other and each independently aryl having 6 to 20 carbon atoms or alkyl having 1 to 20 carbon atoms, of which one or more hydrogen atoms are unsubstituted or substituted by a halogen group, a hydrocarbon group having 1 to 20 carbon atoms, alkoxy, or phenoxy.

11. A method of preparing an olefin polymer by using the catalyst composition of claim 9.

12. A method of preparing an olefin polymer by using the catalyst composition of claim 10.

* * * * *